(12) United States Patent
Mihalef et al.

(10) Patent No.: US 12,198,813 B2
(45) Date of Patent: Jan. 14, 2025

(54) SYSTEM AND METHOD FOR HEART STRAIN DETERMINATION

(71) Applicant: Siemens Healthineers AG, Forchheim (DE)

(72) Inventors: Viorel Mihalef, North Brunswick, NJ (US); Tiziano Passerini, Plainsboro, NJ (US); Puneet Sharma, Princeton Junction, NJ (US)

(73) Assignee: Siemens Healthineers AG, Forchheim (DE)

( * ) Notice: Subject to any disclaimer, the term of this patent is extended or adjusted under 35 U.S.C. 154(b) by 470 days.

(21) Appl. No.: 17/657,208

(22) Filed: Mar. 30, 2022

(65) Prior Publication Data

US 2022/0328195 A1 Oct. 13, 2022

(51) Int. Cl.
| | |
|---|---|
| *G16H 50/30* | (2018.01) |
| *G06T 7/00* | (2017.01) |
| *G06T 7/70* | (2017.01) |
| *G06T 17/20* | (2006.01) |

(52) U.S. Cl.
CPC ............ *G16H 50/30* (2018.01); *G06T 7/0012* (2013.01); *G06T 7/70* (2017.01); *G06T 17/20* (2013.01); *G06T 2207/10072* (2013.01); *G06T 2207/20084* (2013.01); *G06T 2207/30048* (2013.01)

(58) Field of Classification Search
CPC ....... G06T 7/11; G06T 7/143; G06V 2201/03; A61B 8/14; A61B 8/463
See application file for complete search history.

(56) References Cited

U.S. PATENT DOCUMENTS

| | | | | |
|---|---|---|---|---|
| 7,127,100 | B2* | 10/2006 | Wenzel | G06V 20/64 |
| | | | | 382/154 |
| 8,068,994 | B2* | 11/2011 | Drăghici | G16B 20/20 |
| | | | | 435/5 |
| 9,679,374 | B2* | 6/2017 | Choi | G16H 50/20 |
| 9,757,036 | B2* | 9/2017 | Strommer | A61B 5/0044 |
| 10,165,960 | B2* | 1/2019 | Forman | G01R 33/4822 |
| 10,198,853 | B2* | 2/2019 | Steen | G06T 15/80 |

OTHER PUBLICATIONS

Nguyen, J., Vezza, M., Mulyala, R. and Singh, H., 2018. Comparison of 2D and 3D Strain Using Cardiovascular Magnetic Resonance Feature Tracking. Journal of the American College of Cardiology, 71(11 Supplement), p. A1603.
Xu, T.Y., Sun, J.P., Wang, X., Wang, D., Li, Y., Lee, A.P.W., Yang, X.S., Wang, J.G. and Yu, C.M., 2013. Comparison Between 2D and 3D Speckle Tracking Echocardiography in Evaluating Left Ventricular Strain of Adults.

(Continued)

*Primary Examiner* — Yosef Kassa (57) ABSTRACT

Heart strain determination includes receiving a series of 2D-slice images as input. A pose estimation module estimates a slicing-pose of the inputted series of 2D-slice images in the heart. A 3D deformation estimation module estimates a 3D deformation field from the series of 2D-slice images and the estimated slicing-pose. A strain measurement module computes a heart strain measure from the 3D deformation field and a predefined definition for strain computation.

20 Claims, 6 Drawing Sheets

(56) References Cited

OTHER PUBLICATIONS

N Park, T., Liu, M.Y., Wang, T.C. and Zhu, J.Y., 2019. GauGAN: semantic image synthesis with spatially adaptive normalization. In ACM SIGGRAPH 2019 Real-Time Live! (pp. 1-1).
Lu, L., Meng, X., Mao, Z. and Karniadakis, G.E., 2019. DeepXDE: A deep learning library for solving differential equations. arXiv preprint arXiv:1907.04502.
Chu, M., Xie, Y., Leal-Taixé, L. and Thuerey, N., 2018. Temporally coherent gans for video super-resolution (tecogan). arXiv preprint arXiv:1811.09393, 1(2), p. 3.
Nasiraei Moghaddam Abbas et al: "Analytical method to measure three-dimensional strain patterns in the left ventricle from single slice displacement data", Journal of Cardiovascular Magnetic Resonance, Biomed Central Ltd, London UK, vol. 12, No. 1, Jun. 2010 (Jun. 2010), p. 33.
Voigt Jens-Uwe et al: "2- and 3-Dimensional Myocardial Strain in Cardiac Health and Disease", JACC: Cardiovascular Imaging, Elsevier, Amsterdam, NL, vol. 12, No. 9, Sep. 2019 (Sep. 2019), pp. 1849-1863.
Edward Ferdian et al: "Fully Automated Myocardial Strain Estimation from CMR Tagged Images using a Deep Learning Framework in the UK Biobank", arxiv.org, Cornell University Library, 201 Olin Library Cornell University Ithaca, NY 14853, Apr. 15, 2020 (Apr. 15, 2020).
Davis M Vigneault et al: "Feature Tracking Cardiac Magnetic Resonance via Deep Learning and Spline Optimization", arxiv.org, Cornell University Library, 201 Olin Library Cornell University Ithaca, NY 14853, Apr. 12, 2017.
Extended European Search Report (EESR) mailed Oct. 1, 2021 in corresponding European Patent Application No. 21167928.7.

\* cited by examiner

FIG 4 Pose Estimator & Out-of-plane Motion Training Setup

Pose Estimator & Out-of-plane Motion Training Setup

SYSTEM AND METHOD FOR HEART STRAIN DETERMINATION

RELATED APPLICATION

This application claims the benefit of 21167928.7, filed Apr. 12, 2021, which is hereby incorporated by reference in its entirety.

FIELD

The present embodiments describe a system and a method for heart strain determination (i.e., the determination of the engineering property called strain of the heart), especially for uncertainty of 2D strain measures and 2D-to-3D strain mapping.

BACKGROUND

Clinically, measurements like longitudinal or circumferential cardiac strain are still being extracted from 2D ultrasound (US) or magnetic resonance imaging (MRI) in many instances, although it has been assessed that 3D strain was better than 2D strain in assessing LV function (see Nguyen, J., et al. "Comparison of 2D and 3D strain using cardiovascular magnetic resonance feature tracking", Journal of the American College of Cardiology, 71(11 Supplement), p. A1603; 2018), while being significantly different, especially for circumferential and radial strain (see Xu, T. Y., et al. "Comparison Between 2D and 3D Speckle Tracking Echocardiography in Evaluating Left Ventricular Strain of Adults", 2013). This is due, on one hand, to the existing large 2D US installation base and a slower upgrade to 3D ultrasound systems, as well as to requirements of high temporal or spatial resolution, which can make it preferred over 3D ultrasound (or, similarly, over 3D MRI).

SUMMARY AND DETAILED DESCRIPTION

However, there are several factors that contribute to errors in such measurements, like foreshortening effects due to misaligned slices or out-of-plane deformations of the heart. This disclosure offers solutions to quantify such errors and inform on the uncertainty of 2D measurements coming from 2D US or MRI data.

While references like the ones mentioned above compare the 2D and 3D strain measurements, there are no existing methods that provide uncertainty measures or corrections for 2D strain, assuming a 3D ground truth.

The errors mentioned above, which are inherent in the measurements due to their essentially 2D nature, would become hidden variables in any clinical study, negatively effecting the predictive value of 2D strain estimations.

So, it is the object to improve the known systems and methods and provide an optimized system and method for heart strain determination.

This object is achieved by the systems, methods, data generation devices, and medical imaging systems herein.

A system and a method are provided for determining a 3D strain of a heart by using a series of 2D-slice images of the heart. Although, these 2D-slice images should show the same 2D area at different times, they also could show a slightly different pose due to movements of the heart or the patient. With the expression "pose," there is meant a position and orientation in space. The present embodiments are especially advantageous for providing a statistical characterization of the 3D strain, which could for example include a mean and a distribution.

A system according to one embodiment, for heart strain determination includes the following components:
  a computing unit (computer), configured to receive a series of 2D-slice images as input, to execute several modules, to pass intermediate result-data from an output of one module to an input of another module and to output a result,
  a pose estimation module, configured to estimate a slicing-pose (orientation and position) of the inputted series of 2D-slice images in the heart,
  a 3D deformation estimation module, configured to estimate a 3D deformation field from a series of 2D-slice images and the estimated slicing-pose,
  a strain measurement module, configured to compute a heart strain measure from the 3D deformation field and predefined definitions for strain computation.

A suitable computing unit should have enough memory and computing power to host the modules. This means that the computing unit is able to process data with these modules in order to get results from input data. However, since there is a sequence of performing acts during the determination process, it is not necessary that all modules are hosted at the same time. Modules could also be present in a static memory and fetched (uploaded in a RAM) by the computing unit when needed. Such computing units, typically having a processor, a static memory, a random-access memory (RAM), a graphics processing unit (GPU), an input interface and an output interface are known in the art. The RAM could be used to host a module while working with it, store the results of a module and feed them to another module. The output interface may be a data interface or a display. Any device for outputting results is possible as long as the device is able to provide the data format desired by the user.

As said above, the 2D-slice images are images from a cross section of the heart. The images form a series because the 2D-slice images have been recorded as a series one after another at different times of the cardiac cycle. It is preferred that they all show the same slicing-pose (position and orientation of a plane). However, by adequate training of the pose estimation module and the 3D deformation estimation module, there could be images from different poses (plane positions and orientations), especially from slight deviations of a main pose (due to heart movements or movements of a patient, e.g., due to breathing). The 2D-slice images should show different phases of the heart cycle (but not necessarily of the same heart cycle or necessarily the whole heart cycle). For example, the images could show a region of the heart cycle between end-diastolic (ED) and end-systolic (ES). In the following, the preferred case is assumed that the 2D-slice images are a sequence showing the same plane at different phases of a heart cycle, which include at least ED and ES.

The pose estimation module estimates the slicing-pose attributes of a series of 2D-slice images, preferably using cardiac-centric coordinate system values (e.g., origin, angles, height, radius) and categorical tags (e.g., long axis, short axis, 2CH, 3CH, 4CH, apical, medial, basal). However, also arbitrary coordinate systems are possible. As said above, the pose is the position and the orientation of the 2D-slice in the heart. This could e.g., be realized with a spatial vector for the position and vectors spanning a plane for the orientation. However, the pose could also be provided by using categorical information (e.g., a label: "2 Chamber view") preferably combined with one or more values related to goodness-of-fitting the label. The pose could e.g., be given as foreshortening scores based on some 3D geometric measures, which evaluate for example how "far" is the slice from "the" 2 Chamber view slice. The pose estimation module is especially a regressor for continuous variables (e.g., level of foreshortening) and a classifier for categorical variables (e.g., label). Various model architectures could be possible, however, a convolutional neural network (CNN) is preferred.

It should be noted that 2D-slice images of the heart look very different from each other, depending on where the image is taken. Different 2D images could have been optimized to look at specific anatomical structures and their motion. It is important to know what region of the heart the 2D-slice image shows, to be able to use the information correctly in the further proceeding. The pose of the 2D-slice image is, in short, a way to define what plane of the heart is shown.

In the 2D-slice images, the heart is only visible as a sequence of pixels characterizing "material" of the heart (the "walls" of the heart). It is preferred that for an easy proceeding, also cardiac contours (endocardium, epicardium, etc.) are also detected within the 2D-slice images by the pose estimation module or, alternatively, by another detection/tracking module specially trained for detecting cardiac contours.

The 3D deformation estimation module estimates a 3D deformation field from a given 2D-slice image sequence (many images or e.g., at least end-diastolic and end-systolic snapshots) and the slicing-pose estimated by the pose estimation module. Especially, the 3D deformation estimation module is also designed for estimating cardiac contours, wherein the deformation field is then preferably given on the 2D slice, along the cardiac contours or along a 3D neighborhood of the contours. Additionally or alternatively, the 3D deformation estimation module is designed to determine a statistical model for the shape of the 3D deformation field. For example, circumferential, radial, and/or longitudinal strains could be estimated. If the 3D deformation field is given in a 3D neighborhood of the contour, other types of strain (e.g., principal, shear etc.) are preferably also provided.

A 3D deformation field is well known in the art as a mathematical concept, with the simplest representation being a vector field (each vector with a 3D origin and a 3D direction), which can be defined for the purpose of an embodiment on the cardiac contour points. In the simple case when data comes from only two cardiac phases, e.g., ED and ES, then the 3D deformation field represents the displacement that deforms an object. This object is deformed such that starting from the configuration corresponding to the first cardiac phase, the object is transformed in the configuration corresponding to the second cardiac phase. In the case in which the data consists in a sequence of 2D slices, the 3D deformation field would be a corresponding sequence of vector fields. A possible, preferred visualization of a 3D-deformation field (e.g., when it is a vector field) is a field of arrows on the slice, especially cutting a 3D model of the heart. A series of 3D-deformation fields (3D and time) is also possible with a temporal series (sequence) of 2D-slice images. The 3D-deformation field may only be determined in a region around the 2D-slice image (especially on the contour of the heart shown in the image) or for the whole heart (e.g., simulated based on the contour of the heart shown in the image).

It should be noted that the deformation is a direct measure for the motion of the heart, since the deformation is a representation of the motion in static images. Thus, it could be imagined that the deformation field characterizes the heartbeat.

Concerning the 3D-deformation field, in-plane- and out-of-plane deformation evaluation is possible. Any in-plane deformation could be characterized by a 2D (only) deformation field. The 3D deformation estimation module is preferably designed to output data of 3D-deformation fields from the 2D (in-plane) deformation. So out-of-plane motion could be provided as a special embodiment of a 3D-deformation field.

The 3D-deformation field is an input to the strain measurement module, which gives the final results. It is preferably designed to calculate a result of the group including 2D strain, 2D "apparent" strain (defined using at all times the cardiac contours of the 2D slices of the 3D meshes), 3D "true" strain (measured on the deforming 3D mesh), and estimated means and statistical distributions of the deformation.

The strain measurement module could be based on a machine learning model or on a conventional algorithm. Preferably, the strain measure module is a geometric computation module for computing a heart strain measure from the 3D-deformation field and predefined definitions for strain computation. The strain measurement module receives as an input the 3D deformation field (given, e.g., as a mean and/or standard deviation 3D vector field) and which uses predefined (e.g., the standard) definitions for strain computation. For example, for a 1D (line) object, the strain would be the relative change in length between two states, e.g., its change of length divided by its original length. In this case, the strain measurement module is preferably designed for determining the relative change in length between two states, e.g., its change of length divided by its original length. For materials, the strain measurement module preferably is a symmetric 3-tensor. Especially, there are standard definitions of longitudinal, radial, and circumferential strains for the heart represented as a thick ellipsoid-like geometric object. Concerning a simple and nevertheless effective strain measurement module, there is no training involved, but rather a simple application of standard strain definitions (e.g., radial) to the deformation field.

The output is preferably a 3D-strain of a 2D cross-section of the heart (e.g., 3D-arrows on a 2D-loop), however, the output could also be a 3D-strain of a 3D-region around a 2D-cross-section of the heart or a 3D-strain of a whole heart. So, the system always provides a 3D-strain, and especially added statistical associated info, e.g., mean and standard deviation, for an area including a 2D cross-section of the heart.

In summary, an embodiment solves the problem of estimating the motion of the heart (by its deformations during the cardiac cycle) and measuring its strain. The preferred way to do this in the state of the art is by acquiring 3D-images of the heart over time, and trace the motion of multiple material points belonging to the heart. This requires several high-resolution 3D-images of the heart which may not be easy to acquire. However, this embodiment is able to get the results from simple 2D-slice images of the heart recorded over time, with specific poses (recognized by the pose estimation module), and trace the motion of material points identified within those 2D-slice images (with the 3D deformation estimation module). The advantage is that the system is capable to estimate a 'true' 3D deformation using only 2D-slice images (that are commonly used in clinical practice).

The pose estimation module can be useful as an instant feedback to the medical operator to choose the most appropriate slice for the type of examination intended. For example, if a 4CH is intended, an optimal angle correction could be suggested to the operator. Alternatively, it could be used for an automatic adjustment sent back to a feedback-controlled probe (in the case of US) or the MRI machine (in the case of MR).

The out-of-plane 3D deformation estimation module provides the 3D-deformation field and values for strain measures. The strain measurements go beyond what the current technologies can provide, in that they are not standard 2D-strains, but they have associated "real" 3D-strains (due to the work of the 3D deformation estimation module).

The method according to one embodiment, for heart strain determination with a system includes the following acts:

Providing a series of 2D-slice images of a cross section of a heart that are recorded at different times. As already said above, it is preferred that they all refer to the same pose. However, there could also be images from different poses (planes), especially from slight deviations of a main pose (due to heart movements or movements of a patient, e.g., due to breathing). The 2D-slice images should show different phases of the heart cycle (but not necessarily of the same heart cycle or necessarily the whole heart cycle). For example, the images could show a region of the heart cycle between end-diastolic (ED) and end-systolic (ES). In the following, the preferred case is assumed that the 2D-slice images are a sequence showing the same cross section at different phases of a heart cycle.

Determining an evaluation of a slicing-pose of the 2D-slices, by inputting the 2D-slices in the (trained) pose estimation module. In the preferred case that all 2D-slice images show (nearly) the same plane, this is preferably a single slicing-pose of all slices. The pose preferably contains a label (e.g., 2 Chamber view) and/or preferably one or more values (e.g., one could be a foreshortening score, which evaluates for example the distance of the slice from a "standard" 2 Chamber view slice). The determination is made automatically by processing the 2D-slice images with the pose estimation module.

Determining a 3D-deformation field, by inputting the 2D-slice images and the evaluated slicing-pose in the (trained) 3D deformation estimation module. The determination is made automatically by processing the 2D-slice images and the slicing-pose with the 3D deformation estimation module. The inputting could be performed automatically with the computing unit that is designed for passing result-data from the output of one module to the input of another module.

Determining a 3D-strain, by inputting the determined 3D-deformation field in the measurement module. Due to the design of the measurement module, the determination is performed automatically. The input could be performed automatically with the computing unit that is designed for passing result-data from the output of one module to the input of another module.

The method preferably includes the additional act of detecting cardiac contours, especially the endocardium and/or the epicardium within the 2D-slice images, especially before determining a 3D-deformation field. The 3D-deformation field is preferably determined for the detected cardiac contours (especially only).

The pose estimation module and the 3D deformation estimation module are preferably two neural networks that are trained with specially prepared data.

A data generation device according to one embodiment is especially designed for generating data for training (and especially also to train) the pose estimation module as well as the 3D deformation estimation module. The training is preferably not performed together, since the pose estimation module is preferably trained first and then the 3D deformation estimation module is trained, since it needs the slicing poses determined by the pose estimation module. However, the outputs of the pose estimation module could also be simulated and these simulated values can be used for validating the outputs of the pose estimation module during training and also be used as inputs of the 3D deformation estimation module during training. The data generation device may furthermore also be used for testing or validation, which is another part of building suitable neural network models.

A data generation device according to one embodiment includes the following components:

A data-conditioning unit (processor) configured to condition and output conditioned 3D+time image sequences of a heart, 3D cardiac chamber masks, and cardiac chamber meshes to a slicing unit of the data generation device. The expression "3D+time" means that there is information about a 3D image as well as there is time information (i.e., movement information). For example, a 3D video showing a model of a beating heart would be a possible 3D+time image sequence. The data-conditioning unit includes a data interface and a generation unit. Since the data-conditioning unit is preferably used to generate its output data from real images of a heart, especially from US or MRI images, as well as generating output data of a synthetic heart, the data interface and the generation unit may have two modi of performance. However, they could also be used for one of these two alternatives, only.

(a) In the case, the conditioned 3D+time image sequences are based on images of a real heart, the data interface is designed for receiving scan data of a heart in form of 3D+time image sequences. These 3D+time image sequences are especially ultrasound data or magnetic resonance imaging data. The generation unit is then designed to generate 3D cardiac chamber masks and cardiac chamber meshes based on the 3D scan data and 3D deformation fields. The "chamber masks" include information about the pixels belonging to the heart in the images. The "chamber meshes" include information of a 3D-surface-mesh model (also including a point-cloud) of the heart shown in the images and 3D image features image features, especially continuous (e.g., coordinate-specific like heart model origin, radius, angles) and/or categorical (long-axis, apical, 2CH, etc.). The 3D deformation fields include information about the movement of the heart over time. These 3D deformation fields are determined based on the 3D scan data, and are preferably directly extracted from these images by a detection/tracking algorithm.

In order to obtain strain, point correspondences between consecutive frames of the series of 2D-slice images is very advantageous. In order to establish such point correspondences, a topology is used that is consistent over time, for example meshes (with constant triangle indices over time), or point clouds (with constant indices over time), or some kind of spatial features that are consistent over time. Indeed, if the feature information is rich enough to characterize the whole heart surface (endo- or epicardium), that would be enough to combine with the masks. But the masks in themselves have no such information, because the number of voxels changes from frame to frame.

(b) Alternatively, or additionally, in the case synthetic conditioned 3D+time image sequences are generated, the data interface is configured for receiving 3D deformation fields form a predefined library and predefined 3D cardiac chamber masks, and especially also cardiac chamber meshes. The generation unit is in this case designed for rendering synthetic 3D+time synthetic image sequences from 3D cardiac chamber masks and 3D deformation fields, and especially also from cardiac chamber meshes. The synthetic 3D+time synthetic image sequences are especially rendered by using 3D images rendered by a GauGAN or TecoGAN algorithm.

The result is always a 3D representation of a beating heart including additional information about 3D image features.

The data generation device further includes:

A slicing unit, designed for generating 2D-slice images from the 3D+time image sequences received from the data-conditioning unit along a predefined plane. For effectively training the pose estimation module with slices taken from a vast number of possible poses, a single 3D+time image sequence is preferably sliced multiple times along a plurality of different predefined planes.

A sampling unit, designed for sampling features of interest (continuous or categorical) onto slices. This unit can be part of the slicing unit. Sampling here means "associated" with the slices, e.g., features of interest that are defined as fields on the 3D image. For example, the "height" of the heart, which is 0 at all the points (voxels) lying in a plane containing the apex and increases in the "upper" longitudinal direction. Or 2D chamber view which would cover a certain region of the 3D image (being 1 in region and 0 outside region). Features from meshes or point clouds can also be "smeared" (i.e., extrapolated from the meshes or point clouds onto the 3D image domain) onto the 3D image and then "sampled" onto any 2D slice.

Optionally: A training unit designed for training a pose estimation module and a 3D deformation estimation module, both modules based on neural networks. Training of neural networks is well known in the art. Suitable training procedures depend on the architectures of the used networks and an artisan knows which training procedure should be applied for the used neural networks. However, it is preferred that the pose estimation module is a CNN and/or the 3D deformation estimation module is a PINN. The training is performed with the 2D-slice images generated by the slicing unit as training data and the 3D deformation fields, the cardiac chamber meshes as well as the conditioned 3D+time image sequences as ground truth.

It should be noted that although the training is based on a slice, a 3D "out-of-plane" deformation is calculated by the 3D deformation estimation module (i.e., a deformation of the slice points, or of some neighborhood of the slice). For that the 3D deformation fields and the 3D cardiac chamber masks/meshes are preferably used as ground truth for validating the results. The ground truth for training is preferably a portion (e.g., 90%) of the data cases created by the data generation device (where each case refers to a different heart), with the other 10% cases used for testing.

Thus, the pose estimation module and the 3D deformation estimation module are trained with specially prepared data. The data generation device starts from previously generated 3D cardiac chamber masks or generates them from input 3D scan data (US or MRI). A 3D deformation field is either directly extracted from images by detection/tracking algorithms or instantiated from a (possibly parameterized) motion library built from such fields. The deformation field is applied on one hand to the masks to generate moving masks and corresponding cardiac surface meshes, and on the other hand it is preferably used to inform a GauGAN or a TecoGAN algorithm for generating synthetic 3D+time image sequences (preferably in US or MRI style). For GauGAN see e.g., N. Park et al. "GauGAN: semantic image synthesis with spatially adaptive normalization", in ACM SIGGRAPH 2019 Real-Time Live! (pp. 1-1); 2019). For TecoGAN see Chu, M. et al. "Temporally coherent gans for video super-resolution (tecogan)", arXiv preprint arXiv: 1811.09393, 1(2), p. 3; 2018. Slicing is then used to generate temporal sequences of 2D images and their corresponding contours.

Regarding the pose estimation module, it is preferred that cardiac-centric coordinate system values, e.g., origin, angles, height, radius, and categorical tags, e.g., long axis, short axis, 2CH, 3CH, 4CH, apical, medial, basal, are used to train this module, that preferably has the architecture of a convolutional neural network (CNN). The trained pose estimation module is used to characterize the slicing-pose of a 2D-slice image in the system and preferably also for training the 3D deformation estimation module.

During training, it is preferred to start with a 3D image sequence representing one or more heart chambers, together with the corresponding anatomical models for each chamber. The anatomical model of one chamber is defined for instance as a triangulated surface whose points are located at the 3D position of the chamber endocardium. As described above, the data generation device creates such pairs of 3D images and corresponding anatomical models. These anatomical models are preferably a combination of meshes and masks (ideally), or point clouds and masks, or feature points and masks.

The triangulated surface is preferably parameterized based on a cardiac-centric reference system built from the chamber geometry. For instance, considering the left ventricle (LV), three orthogonal axes of the reference system can be defined as the long axis of the left ventricle (line connecting the LV apex to the barycenter of the mitral annulus), the axis connecting the barycenter of the mitral annulus with the barycenter of the tricuspid valve, and a third axis orthogonal to the previous two.

Based on this reference system, triangulated surfaces derived from different 3D images are preferably parameterized in the same way. Also based on this reference system, any cutting plane representing the plane of a 2D image can be labeled depending on what parts of the chamber it intersects. For instance, a cutting plane orthogonal to the chamber long axis represents a short axis view; medial/apical/basal regions can be defined based on the point coordinates along the long axis, and correspondingly the cutting plane can be defined a medial/apical/basal short axis view. The same construct extends to other views. Additional labels can be extracted to describe non-standard imaging view: for instance, if the cutting plane intersects the triangulated surface both in medial and apical regions, the view can be labeled as 'foreshortened.' A level of foreshortening could be defined for instance considering the intersection points and computing the complement to the ratio of number of points from a target cardiac region over the total number of intersection points. It is preferred that the meshes include the labels, which themselves can e.g., be divided into the 17 AHA heart segments.

The training set for the pose estimation module (especially in form of a CNN) is then preferably a set of 'image, label' pairs, where the image is obtained by intersecting the original 3D image with the cutting plane; and the label is obtained using for instance the approach described above.

Multiple labels can be associated to each image, and one or multiple neural networks can be trained to perform a classification or a regression task. For instance, a first network can be trained to classify one in multiple possible 2D-views (e.g., 2CH, 3CH, 4CH, SAX), while a second network can be trained to regress the level/severity of the foreshortening. In this case, preferably both networks together form the pose estimation module.

Regarding the training of the 3D deformation estimation module, it is preferred that this module has the architecture of a physics informed neural network (PINN, see Lu, L. et al. "DeepXDE: A deep learning library for solving differential equations", arXiv preprint arXiv:1907.04502; 2019). This module is trained in order to generate a 3D deformation field in the 3D neighborhood of any cardiac contour. The training input uses a given 2D image sequence and the associated cardiac contours and estimated slicing-pose. The deformation field can be further characterized using a statistical model.

According to a preferred embodiment, the training set is defined based on synthetically generated motion fields. In this case, one or more anatomical models representing one or more cardiac chambers are built based on statistical shape models or based on shape templates or using segmentation from images. The anatomical models are then deformed by applying a displacement field (a 3D deformation field) representing the motion of the heart chambers over one or multiple cardiac cycles. The displacement field can be defined based on analytical motion models (e.g., the trajectory followed by each point that is defined a priori as a planar or non-planar ellipse), statistical motion models (e.g., based on observed motion extracted from medical images using tracking algorithms), or computational models (e.g., electromechanical models of the heart). To each anatomical model, one or multiple motion models can be applied. This results in an arbitrarily large database of realistic 3D+time heart chamber geometries.

For each 3D+time chamber geometry, several cutting planes are preferably considered, representing the imaging plane of a 2D image. The intersection of the 3D+time chamber geometry and the cutting plane results in a 2D+time chamber contour, to which a 3D motion field is preferably associated. In other words, in this case, each point on the 2D+time contour is associated to the value of the 3D+time motion field (displacement, velocity) at that location.

Additionally, each point on the 2D+time contour is preferably also associated to its motion in the 2D cutting plane. This is the observable motion in the 2D imaging, that is used to determine 2D strain.

For each 2D+time contour, a 3D bounding box is preferably defined (especially fixed in time), that contains the contour points over the entire time sequence and extends out of the cutting plane. The problem is then preferably formulated as the estimation of the 3D motion of points in the bounding box, given as input the observed (in-plane) motion of the contour points on the slice. It is preferably solved by training a system to accept as input a bounding box defined as described above, that can be discretized as a regular grid of voxels. Voxels corresponding to the position of points belonging to the 2D+time contour are associated with the observed (in-plane) motion field.

Preferred ground truth labels are the values of the 3D+time motion field (i.e., the 3D deformation field) in all voxels of the bounding box.

To regularize the problem, a PINN is preferred, solving the regression problem while respecting the underlying law of motion of an elastic body. The advantage of this approach is implicitly forcing the network to prefer solutions that satisfy a global relationship valid in 3D space for bodies with a given mechanical behavior. Natural extensions of this approach include considering different motion laws in the PINN, such as hyperelastic or viscoelastic.

In a preferred embodiment, hybrid active and passive material laws can be considered, according to which the motion of the body is determined by the interplay of actively generated contraction and passive resistance to motion. In this embodiment, an additional input is preferably provided to the network in the form of a scalar field defined in the bounding box, and assuming nontrivial values in correspondence of the 2D+time contour points. This scalar field represents the time of activation of the cardiac muscle, a determinant of the cardiac motion. Time of activation could be derived for instance from ECG signals paired to the 2D images. In the training process, time of activation could be defined a priori or derived from the computational model used to generate the 3D motion.

A natural extension of the system is the support for multiple 2D slices as an input. The design of the different modules would not change besides obvious modifications e.g., to the definition of the 'bounding box.'

A method according to one embodiment is provided for manufacturing a system (training the pose estimation module and/or the 3D deformation estimation module). For the method, a data generation device is preferably used for training the pose estimation module and/or the 3D deformation estimation module of the system. Particularly, a trained pose estimation module is used for training the 3D deformation estimation module (at least for providing the data for the training). The method includes the following acts: (a) Provide (i.e., download, receive or generate) multiple datasets of different 3D+time image sequences, each of the 3D+time image sequences showing a number of cycles of a beating heart. These 3D+time image sequences include 3D data of a beating heart over a certain time period (e.g., a number of heart cycles). The 3D+time image sequences may show a real heart or they could also be synthetically generated. (b) Provide (i.e., download, receive or generate) 3D cardiac chamber masks and cardiac chamber meshes, each combined with a 3D+time image sequence. Such masks and meshes are described above. with each 3D+time image sequence there is combined a 3D cardiac chamber mask and a cardiac chamber mesh.

Regarding the nature of and the combination between 3D+time image sequences and 3D cardiac chamber masks and cardiac chamber meshes, there are two preferred alternatives that could be used alone or together. There could be 3D+time image sequences based on images of a real heart or synthetic 3D+time image sequences.

In one embodiment, 3D+time image sequences based on images of a real heart, especially ultrasound data or magnetic resonance imaging data, are used and provided for the method. For each received 3D+time image sequence, a corresponding 3D deformation field is generated by tracking the embodiment of the heart in the images and a corresponding 3D cardiac chamber mask as well as a cardiac chamber mesh is derived.

Alternatively, or additionally, 3D deformation fields are received from a predefined library and predefined 3D chamber masks are received, and preferably also cardiac chamber meshes are received. Based on these, corresponding synthetic 3D+time image sequences are generated based on a 3D deformation field, a 3D chamber mask, and especially also a cardiac chamber mesh, especially by using a GauGAN or TecoGAN algorithm. For generating 3D+time image sequences, one 3D deformation field could be combined with multiple different masks and/or meshes, and/or one cardiac chamber mesh could be combined with multiple different deformation fields and/or masks, and/or one 3D cardiac chamber mask could be combined with multiple different deformation fields and/or meshes.

(c) Slicing a 3D+time image sequence along a predefined plane to form a 2D-slice image and adding features to the 3D slice image based on the 3D cardiac chamber mask and chamber mesh combined with this 3D+time image sequence. It is clear that for training, this slicing act must be performed many times to get a vast amount of 2D-slice images. To achieve that, it is preferred to use many 3D+time image sequences, but also perform different slicing procedures for any 3D+time image sequence.

(d) Training a pose estimation module and/or a 3D deformation estimation module of the system by using the sliced 3D+time image sequence as training data and a ground truth based on the 3D+time image sequence and the 3D cardiac chamber mask and the chamber mesh combined with this 3D+time image sequence. Training of neural networks is well known in the art. Preferably, all the data (all the cases) is ground truth, but in terms of training/testing it, is especially split in e.g., 90% of cases for training an 10% for testing.

For example, a cardiac mesh could be created and provided for the method. Then, a 3D deformation field could be downloaded from a library and a deformation of the mesh in time could be calculated based on the deformation field. Then, the mesh could be rendered with GauGAN or Teco-GAN to get an artificially rendered, beating heart. This would result in a synthetic 3D-time image sequence ready to be sliced. This is an easy approach based on the case that the GauGAN/TecoGAN generated series would be temporally consistent, namely consecutive frames would have a reasonably small change in the generated image (consistent with the cardiac deformation. Other possible methods are explained above. When using rendering algorithms (e.g., GauGAN) to generate realistic moving 3D-images, 3D cardiac chamber masks and 3D deformation fields are preferably used as input, and the 3D cardiac chamber masks are conditioned by the deformation fields as an additional feature.

Preferably, the 2D-slice images are segmented to get segmented contours of the heart, e.g., endocardium or epicardium. Additional features are also preferred, e.g., continuous features (e.g., coordinate-specific like origin, radius, angles) and/or categorical features (e.g., long axis, short axis, 2CH, 3CH, 4CH, apical, medial, basal).

It is especially preferred to train the 3D deformation estimation module with results from a (trained) pose estimation module.

A control device (controller) according to one embodiment for controlling a medical imaging system, especially an ultrasound system or a magnetic resonance imaging system, includes the system. Alternatively, or additionally, the controller is designed to perform the method. The control device may include additional units (processor implemented modules) or devices for controlling components of a medical imaging system.

A medical imaging system, especially an ultrasound system or a magnetic resonance imaging system, includes a system according to one of the embodiments.

Some units or modules of the system or the control device mentioned above can be completely or partially realized as software modules running on a processor of a system or a control device. A realization largely in the form of software modules can have the advantage that applications already installed on an existing system can be updated, with relatively little effort, to install and run these units of the present application. The object is also achieved by a computer program product with a computer program that is directly loadable into the memory of a device of a system or a control device of a medical imaging system, and which includes program units to perform the acts of the method when the program is executed by the control device or the system. In addition to the computer program, such a computer program product can also include further parts such as documentation and/or additional components, also hardware components such as a hardware key (dongle etc.) to facilitate access to the software.

A non-transitory computer readable storage medium, such as a memory stick, a hard-disk or other transportable or permanently-installed carrier, can serve to transport and/or to store the executable parts of the computer program product so that these can be read from a processor unit of a control device or a system. A processor unit can include one or more microprocessors or their equivalents.

Particularly advantageous embodiments and features of the invention are given by the dependent claims, as revealed in the following description. Features of different claim categories may be combined as appropriate to give further embodiments not described herein.

According to a preferred system, the pose estimation module and/or the 3D deformation estimation module is a machine learning model, especially a deep learning model, particularly preferably a neuronal or neural network. The pose estimation module is preferably a convolutional neural network (CNN) that is trained for estimating the pose of a 2D-slice image in the heart. The 3D deformation estimation module is preferably a physics-informed neural network (PINN) that is trained for estimating a 3D-deformation field from a plurality of 2D-slice images and a given slicing-pose of these 2D-slice images.

As said above, it is preferred that the 3D deformation estimation module has been trained with results of the pose estimation module, preferably wherein the pose estimation module as well as the 3D deformation estimation module have been trained with the same data generation device.

Preferably, the 3D-deformation estimation module is designed for additionally determining a statistical model for the deformations of the 3D deformation field and/or for estimating cardiac contours, e.g., epicardium or endocardium. Preferably, the 3D-deformation estimation module is designed for additionally determining a 3D deformation field on the 2D slice along the cardiac contours or along a 3D neighborhood of the contours.

Preferably, the strain measurement module is a geometric computation module that is designed to receive as an input the 3D deformation field and to use predefined (e.g., standard) definitions for strain computation. It is preferred that the strain measurement module is designed for calculating the relative change of a strain as a change in length between two states, e.g., its change of length divided by its original length. Alternatively, or additionally, the strain measurement module computes preferably a symmetric 3-tensor.

Preferably, the pose estimation module or an additional detection module is specially trained (or contains the capability from an external module) for detecting cardiac contours, especially the endocardium and/or the epicardium, within the 2D-slice images.

In a preferred system according to one embodiment, components of the system are part of a data-network, wherein preferably the data-network and a medical imaging system (especially an ultrasound system or a magnetic resonance imaging system which provides image data) are in data-communication with each other, wherein the data-network preferably includes parts of the internet and/or a cloud-based computing system, wherein preferably the system or a number of components of this system is realized in this cloud-based computing system. For example, the components of the system are part of a data-network, wherein preferably the data-network and a medical imaging system, which provides the image data, are in communication with each other. Such a networked solution could be implemented via an internet platform and/or in a cloud-based computing system.

The method may also include elements of "cloud computing." In the technical field of "cloud computing," an IT infrastructure is provided over a data-network, e.g., a storage space or processing power and/or application software. The communication between the user and the "cloud" is achieved by data interfaces and/or data transmission protocols.

In the context of "cloud computing," in a preferred embodiment of the method, provision of data via a data channel (for example a data-network) to a "cloud" takes place. This "cloud" includes a (remote) computing system, e.g., a computer cluster that typically does not include the user's local machine. This cloud can be made available in particular by the medical facility, which also provides the medical imaging systems. In particular, the image acquisition data is sent to a (remote) computer system (the "cloud") via a RIS (Radiology Information System) or a PACS (Picture Archiving and Communication System).

Within the scope of a preferred embodiment of the system, the abovementioned modules and units are present on the "cloud" side. A preferred system further includes, a local computing unit (computer) connected to the system via a data channel (e.g., a data-network, particularly configured as RIS or PACS). The local computing unit includes at least one data receiving interface to receive data. Moreover, it is preferred if the local computer additionally has a transmission interface in order to send data to the system.

The advantages could be two-fold. On the one hand, an enhanced efficiency for US or MR systems is provided using 2D scanning protocols which do not perfectly align with the intended slice orientation. On the other hand, it is provided an improved clinical value of strain values and increased customer trust. The key algorithms rely on machine learning of the slicing-pose of a 2D image, and of the 3D deformation field around the 2D cardiac contour, which allow an enhanced characterization of a 2D image-based strain with learned 3D strain values.

BRIEF DESCRIPTION OF THE DRAWINGS

Other objects and features of the present invention will become apparent from the following detailed descriptions considered in conjunction with the accompanying drawings. It is to be understood, however, that the drawings are designed solely for the purposes of illustration and not as a definition of the limits of the invention.

In the diagrams, like numbers refer to like objects throughout. Objects in the diagrams are not necessarily drawn to scale.

DETAILED DESCRIPTION OF THE PREFERRED EMBODIMENTS

Figure 1:
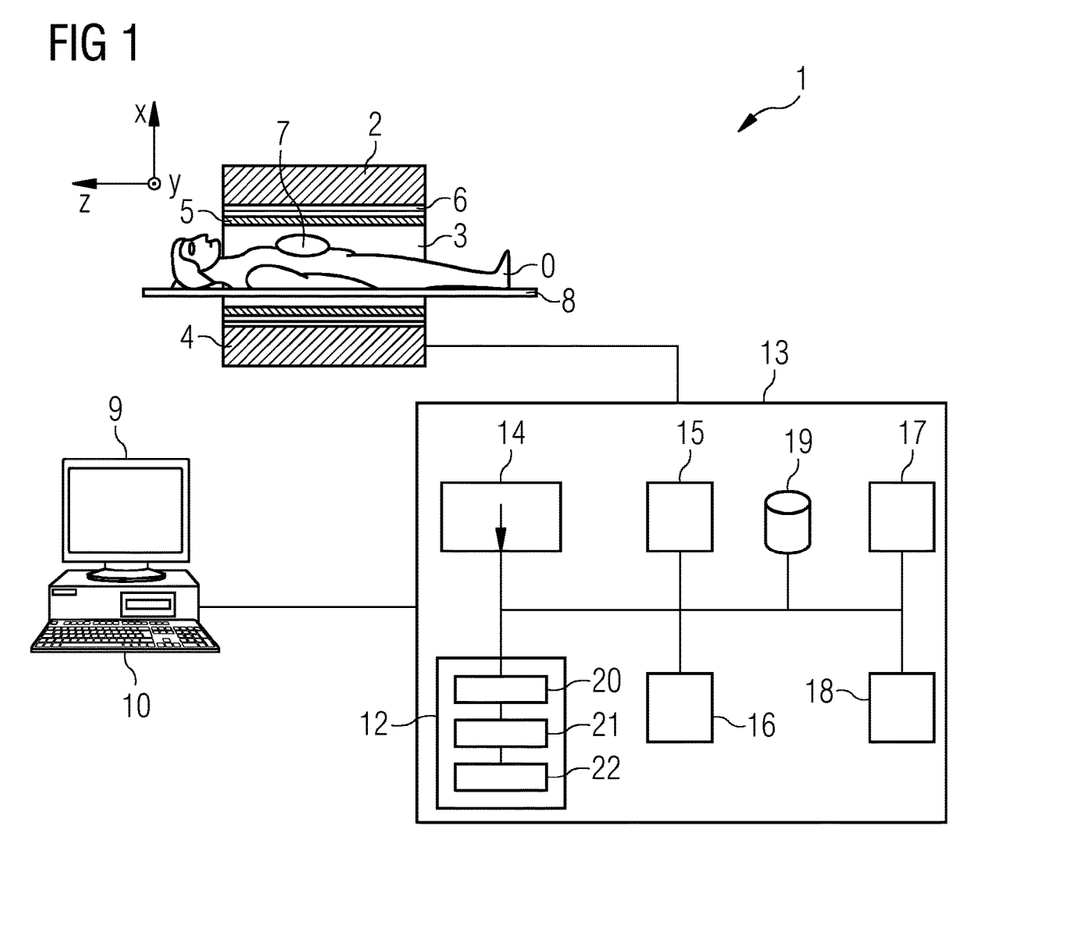
FIG. 1 shows a simplified MRI system according to an embodiment.

FIG. 1 shows a schematic representation of a magnetic resonance imaging system 1 ("MRI-system") as an example for a medical imaging system 1. The MRI system 1 includes the actual magnetic resonance scanner (data acquisition unit) 2 with an examination space 3 or patient tunnel in which a patient or test person 0 is positioned on a driven bed 8, in whose body the actual examination object is located.

The magnetic resonance scanner 2 is typically equipped with a basic field magnet system 4, a gradient system 6 as well as an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as local coils (symbolized here by only a single local coil) to be arranged on the patient or test subject. In principle, however, the whole-body coil can also be used as an RF reception antenna system, and the local coils can respectively be switched into different operating modes.

The basic field magnet system 4 is designed that a 3D image can be recorded. It here is designed in a typical manner so that it generates a basic magnetic field in the longitudinal direction of the patient, i.e., along the longitudinal axis of the magnetic resonance scanner 2 that proceeds in the z-direction. The gradient system 6 typically includes individually controllable gradient coils in order to be able to switch (activate) gradients in the x-direction, y-direction or z-direction independently of one another.

The MRI system 1 shown here is a whole-body system with a patient tunnel into which a patient can be completely introduced. However, in principle, other MRI systems, for example with a laterally open, C-shaped housing, as well as in smaller magnetic resonance scanners in which only one body part, can be provided.

Furthermore, the MRI system 1 has a central control device (controller) 13 that is used to control the MRI system 1. This central control device 13 includes a sequence control unit 14 for measurement sequence control. With this sequence control unit 14, the series of radio-frequency pulses (RF pulses) and gradient pulses can be controlled depending on a selected pulse sequence to acquire magnetic resonance images within a measurement session. It is preferred to acquire 3D images for multiple points of time to provide a 3D+time image sequence IS for training or a 2D-slice image SI. For example, such a series of pulse sequence can be predetermined within a measurement or control protocol. Different control protocols for different measurements or measurement sessions are typically stored in a memory 19 and can be selected by and operator (and possibly modified as necessary) and then be used to implement the measurement.

To output the individual RF pulses of a pulse sequence, the central control device 13 has a radio-frequency transmission device (transmitter) 15 that generates and amplifies the RF pulses and feeds them into the RF transmission antenna system (antenna or coils) 5 via a suitable interface (not shown in detail). To control the gradient coils of the gradient system 6, the control device 13 has a gradient system interface 16. The sequence control unit 14 communicates in a suitable manner with the radio-frequency transmission device 15 and the gradient system interface 16 to emit the pulse sequence.

Moreover, the control device 13 has a radio-frequency reception device (receiver) 17 (likewise communicating with the sequence control unit 14 in a suitable manner) in order to acquire magnetic resonance signals (i.e., raw data) for the individual measurements, which magnetic resonance signals are received in a coordinated manner from the RF reception antenna system (antenna or coils) 7 within the scope of the pulse sequence.

A reconstruction unit 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central control device 13 can take place via a terminal 10 with an input unit (input device) and a display unit (display screen) 9, via which the entire MRI system 1 can thus also be operated by an operator. MR images can also be displayed at the display unit 9, and measurements can be planned and started by the input unit (possibly in combination with the display unit 9), and in particular suitable control protocols can be selected (and possibly modified) with suitable series of pulse sequence PS as explained above.

The control device 13 includes a system 12 designed to perform the method according to one embodiment. The control device 13 acts here as a computing unit (computer) designed to receive 2D-slice images as input (the raw data RD that is reconstructed with the reconstruction unit), to host several modules 20, 21, 22, to pass intermediate result-data from an output of one module 20, 21, 22 to an input of another module 20, 21, 22 and to output the result. The system 12 includes the following components that may be software modules.

- A pose estimation module 20 that is designed to estimate a slicing-pose of the inputted 2D-slice images in the heart. In this example, the pose estimation module 20 is a CNN specifically trained by a data generation device 23 that is here also part of the control device 13.
- A 3D deformation estimation module 21 that is designed for estimating a 3D deformation field DF from a plurality of 2D-slice images SI and the estimated slicing-pose. In this example, the 3D deformation estimation module 21 is a PINN specifically trained by said data generation device 23.
- A strain measurement module 22 that is designed for computing a heart strain measure from the 3D deformation field and predefined definitions for strain computation.

The pose estimation module 20 estimates the 3D "pose" attributes of a sequence of 2D-slice images SI (see following figures), using here cardiac-centric coordinate system values (e.g., origin, angles, height, radius) and categorical tags (e.g., long axis, short axis, 2CH, 3CH, 4CH, apical, medial, basal). In this example, cardiac contours (endocardium, epicardium, etc.) could also detected within this module, or, alternatively, provided by another detection/tracking module.

The 3D deformation estimation module 21 estimates a 3D deformation field DF from a given 2D-slice image sequence (or at least end-diastolic and end-systolic snapshots) and the estimated pose and cardiac contours. The 3D deformation field DF is given here on the 2D-slice images, along the cardiac contours or along a 3D neighborhood of the contours, and it can include a statistical model for the deformations.

The 3D deformation field DF is an input to the strain measurement module 22 which provides here the final results, including 2D strain, 2D "apparent" strain (defined using at all times the cardiac contours of the 2D slices of the 3D meshes), 3D "true" strain (measured on the deforming 3D mesh) and estimated means and statistical distributions of the deformation. This applies for example to circumferential, radial and longitudinal strains. If the deformation field is given here in a 3D neighborhood of the contour, other types of strain (e.g., principal, shear etc.) can also be provided.

The MRI system 1 according to one embodiment, and in particular the control device 13, can have a number of additional components that are not shown in detail but are typically present at such systems, for example a network interface in order to connect the entire system with a network and be able to exchange raw data and/or image data or, respectively, parameter maps, but also additional data (for example patient-relevant data or control protocols).

The manner by which suitable raw data are acquired by radiation of RF pulses and the generation of gradient fields, and MR images are reconstructed from the raw data, is known to those skilled in the art and thus need not be explained in detail herein.

Figure 2:
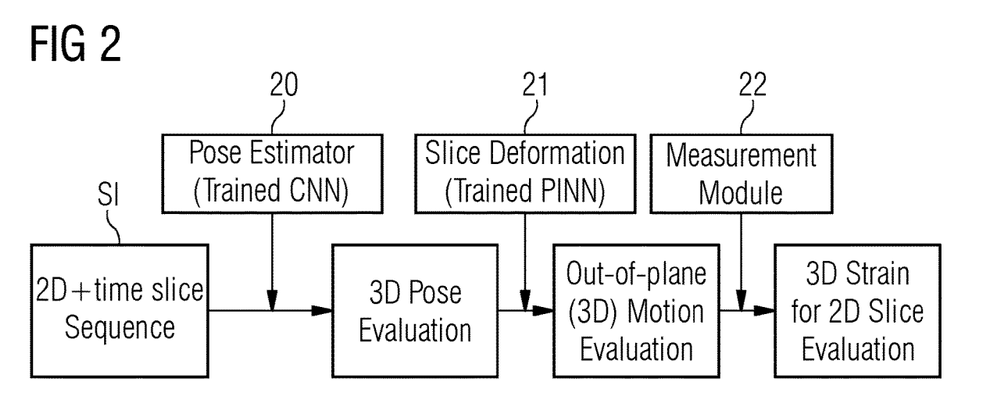
FIG. 2 depicts the process flow of a preferred method according to one embodiment.

FIG. 2 depicts the process flow of a preferred method according to one embodiment for heart strain determination with a system 12 as e.g., shown in FIG. 1. Horizontal arrows indicate data flow, and vertical arrows indicate processing of the data.

First (left), a series of 2D-slice images SI of a cross section of a heart that are recorded at different times are provided. In this example, it is a 3D+time slice sequence.

From these 2D-slices, an evaluation of a slicing-pose is determined by inputting them in the pose estimation module 20. The output are again the 2D-slices and the results of the pose estimation module 20, i.e., information about the orientation of the plane of the slice in the heart. One gets the "3D pose evaluation".

Next, a 3D-deformation field DF is determined (see e.g., FIGS. 5 and 6) by inputting the series of 2D-slice images SI and the evaluated slicing-pose in the 3D-deformation estimation module 21. The result is the out-of-plane (3D) motion evaluation.

Last, the measurement module 22 determines a 3D-strain for the 2D slice evaluation by calculating measurements of the deformation and comparing it with threshold values.

In addition, cardiac contours could be detected, especially the endocardium and/or the epicardium within the 2D-slice images SI, especially before determining a 3D-deformation field DF. In this case, the 3D-deformation field DF is preferably determined for the detected cardiac contours.

Figure 3:
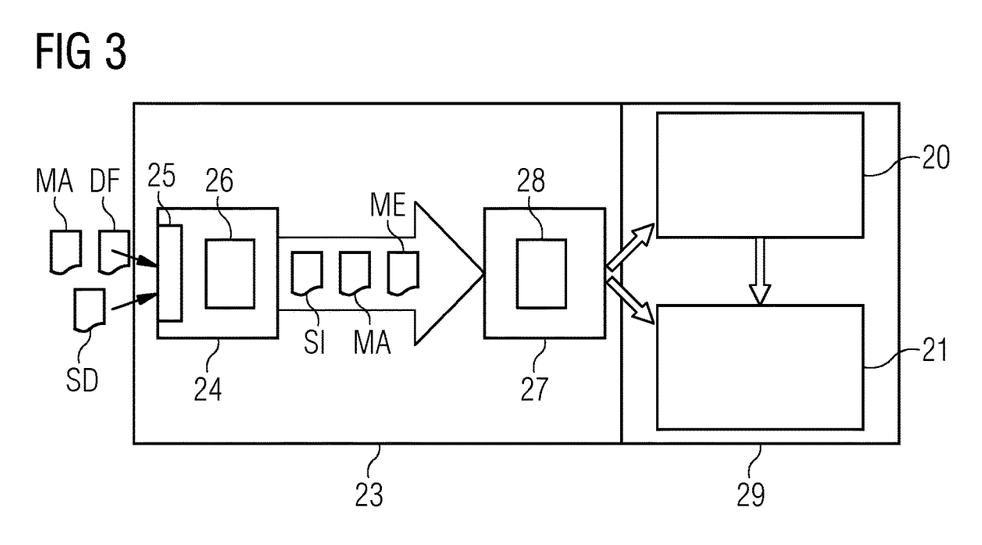
FIG. 3 shows an example of a data generation device.

FIG. 3 shows an example of a data generation device 23 for generating data for training of the pose estimation module 20 and/or the 3D deformation estimation module 21 of a system 12 (see FIG. 1). The data generation device 23 shown here is also designed for training these components with this data. The data generation device 23 includes the following components:

A data-conditioning unit 24 designed to condition and output conditioned 3D+time image sequences IS of a heart, 3D cardiac chamber masks MA and cardiac chamber meshes ME to the slicing unit 27. The data-conditioning unit 24 includes a data interface 25 and a generation unit 26.

There are two preferred use-cases. One (a) where training data is based on 3D+time image sequences IS based on images of a real heart and one (b), where training data is based on synthetic 3D+time image sequences IS.

a) In the case where the conditioned 3D+time image sequences IS are based on images of a real heart, the data interface 25 is designed for receiving scan data SD of a heart in form of 3D+time image sequences IS, especially ultrasound data or magnetic resonance imaging data. The generation unit 26 is designed to generate 3D cardiac chamber masks MA and cardiac chamber meshes ME based on the 3D scan data SD and 3D deformation fields DF determined from the 3D scan data SD.

b) In the case where synthetic conditioned 3D+time image sequences IS are generated, the data interface 25 is designed for receiving 3D deformation fields DF form a predefined library and predefined 3D cardiac chamber masks MA. The generation unit 26 is designed for rendering synthetic 3D+time image sequences IS from 3D cardiac chamber masks MA and 3D deformation fields DF, and especially also from cardiac chamber meshes ME, especially by using a GauGAN or TecoGAN algorithm.

The slicing unit 27 is designed for generating 2D-slice images SI from the (real or synthetic) 3D+time image sequences IS received from the data-conditioning unit 26. The slicing is performed along a predefined plane or there are prepared multiple slices S along different predefined planes from any 3D+time image sequence IS.

Here an additional sampling unit 28 in the slicing unit 27 samples features of interest onto the slices S.

In this example, the data generation device 23 includes a training unit 29 that is designed for training a pose estimation module 20 and a 3D deformation estimation module 21. Both modules 20, 21 are based on neural networks, wherein the pose estimation module 20 is preferably based on a CNN and the 3D deformation estimation module 21 is based on a PINN. The 2D-slice images SI generated by the slicing unit 27 are used as training data and the 3D deformation fields DF, the cardiac chamber meshes ME as well as the conditioned 3D+time image sequences IS are used as ground truth.

Figure 4:
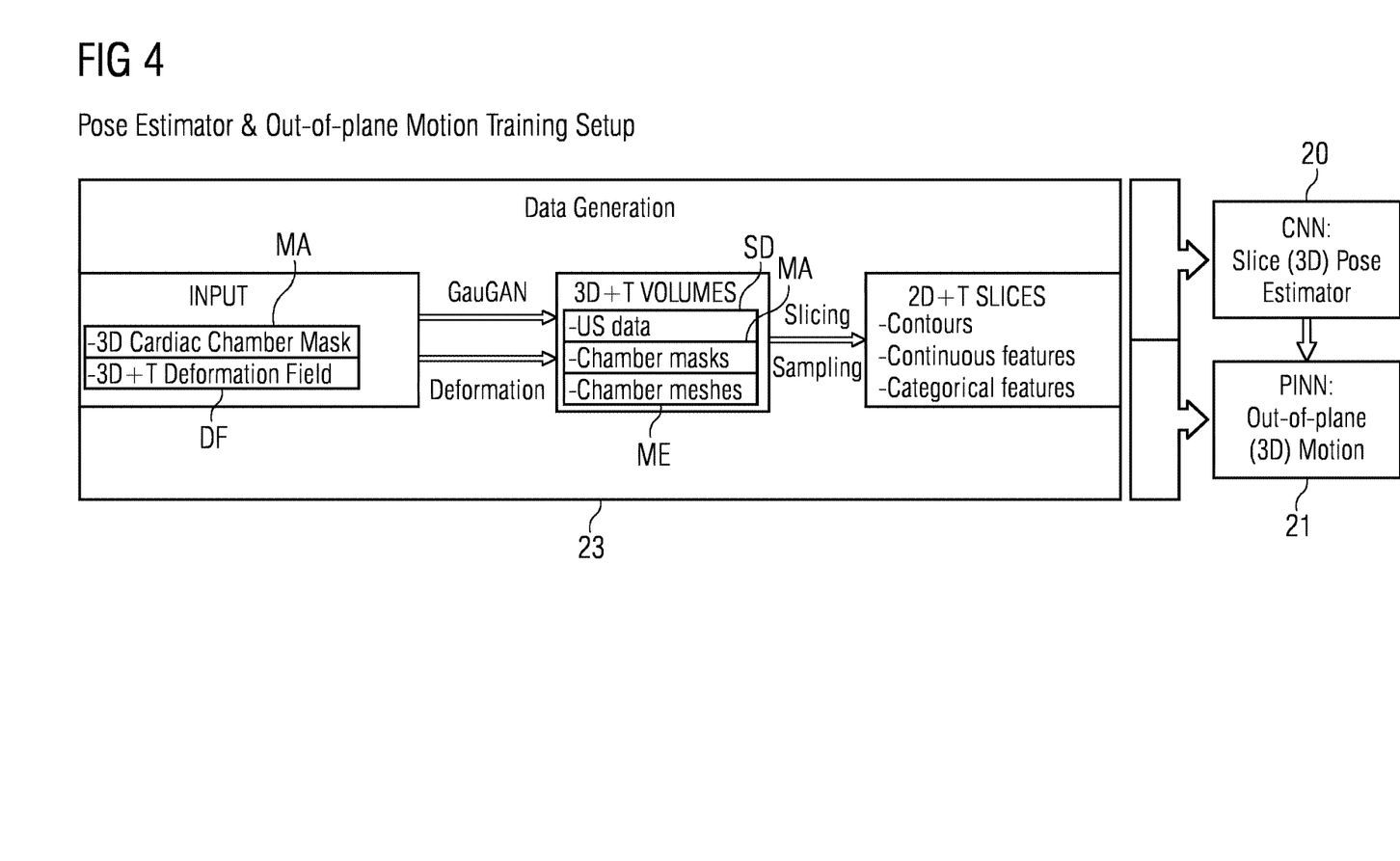
FIG. 4 depicts the process flow of a preferred manufacturing method according to one embodiment.

FIG. 4 depicts the process flow of a preferred manufacturing method according to one embodiment.

There are provided (here generated) multiple datasets of different 3D+time image sequences IS, each of the 3D+time image sequences IS shows a number of cycles of a beating heart.

In the shown case, a synthetic 3D+time image sequence IS (here ultrasound images: "US data") is generated. To achieve that, a 3D cardiac chamber mask MA and a 3D deformation field DF are inputted (left) and with the help of a GauGAN algorithm synthetic ultrasound data is created (the 3D+time image sequences IS) from the input data. Furthermore, cardiac chamber meshes ME are created using the 3D cardiac chamber masks MA and the 3D deformation field DF.

After that, a slicing act follows. A 3D+time image sequence IS is sliced along a predefined plane to form a 2D-slice image SI. Furthermore, features are added to the 2D-slice image SI. These features are here contours, continuous features (e.g., coordinate-specific like origin, radius, angles) and categorical features (long-axis, apical, 2CH, etc.).

Then, indicated by the arrows at the right, a pose estimation module 20 and a 3D deformation estimation module 21 are trained by using the sliced 3D+time image sequence IS as training data and a ground truth based on the 3D+time image sequence IS and the 3D cardiac chamber mask and the cardiac chamber mesh combined with this 3D+time image sequence IS. For the 3D deformation estimation module 21, there are additionally used results of the pose estimation module 20 for training.

Figure 5:
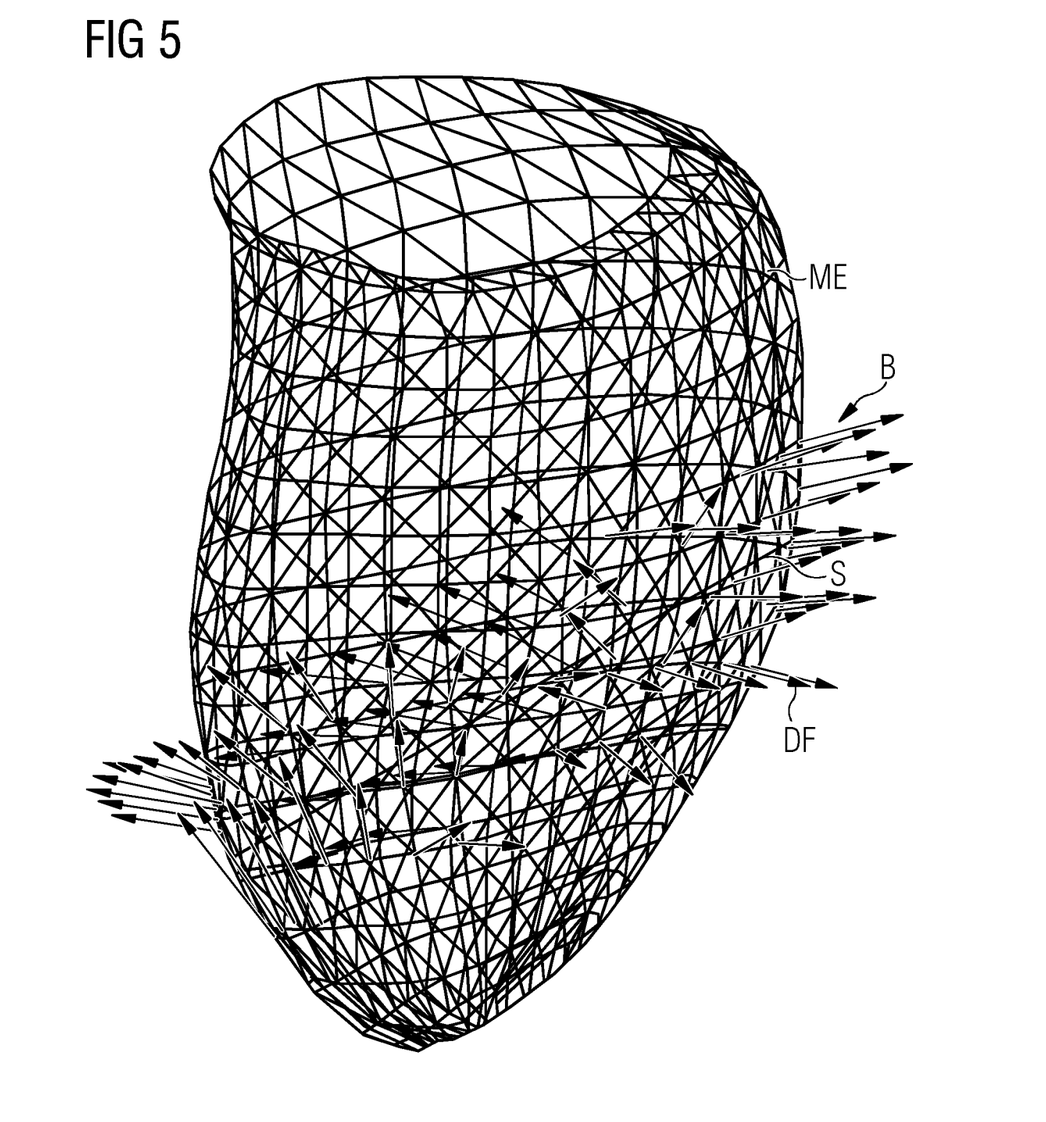
FIG. 5 shows an example perspective view of a mesh model of a heart with a slice and a 3D deformation field.
Figure 6:
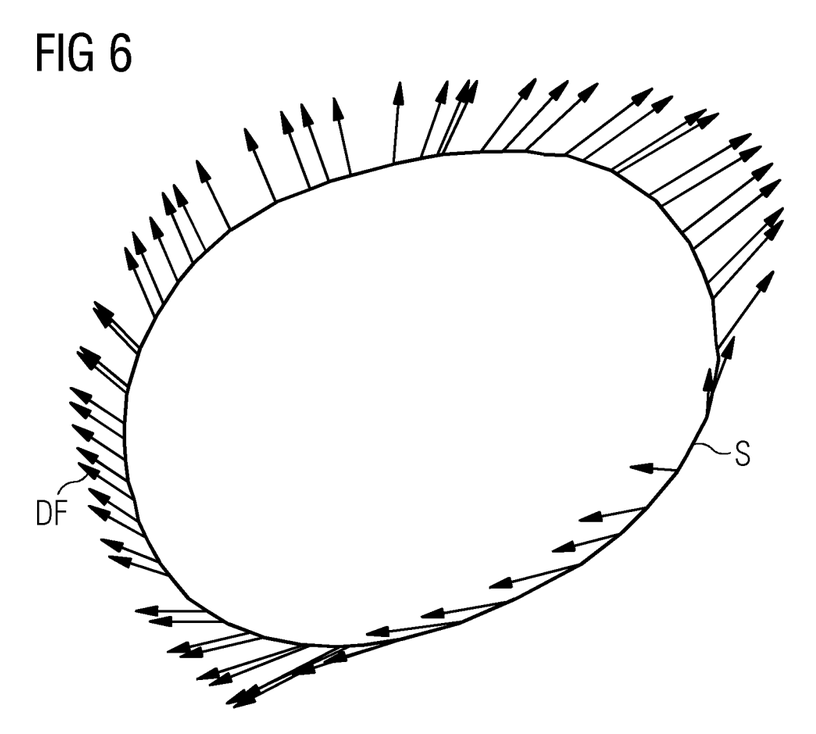
FIG. 6 shows an example top view on a slice and a 3D deformation field.

Using the trained modules, a 3D "out-of-plane" deformation of a slice S can be calculated by the 3D deformation estimation module 21 as shown in FIGS. 5 and 6.

FIG. 5 shows a perspective view of a mesh model of a heart with a cardiac chamber mesh ME and a slice S surrounded by a 3D deformation field DF. FIG. 6 shows a top view of that slice S and the 3D deformation field. Since FIGS. 5 and 6 show an artificial heart, they depict training data. However, these figures can also be used for explaining the use of the system according to one embodiment by imagining the mesh to be a real heart and the slice S in FIG. 6 to be the 2D-slice image SI.

During training, a 3D deformation field DF is either directly extracted from images by detection/tracking algorithms or instantiated from a motion library built from such fields. The deformation field DF is applied on one hand to the 3D cardiac chamber masks MA to generate moving masks and corresponding cardiac chamber (surface) meshes ME. On the other hand, it is here used to inform a GauGAN or a TecoGAN algorithm for generating synthetic 3D+time image sequences (preferably in US or MRI style).

Regarding the pose estimation module 20, it is preferred that cardiac-centric coordinate system values, e.g., origin, angles, height, radius, and categorical tags, e.g., long axis, short axis, 2CH, 3CH, 4CH, apical, medial, basal, are used to train this module. The trained pose estimation module 20 is used to characterize the slicing-pose of a 2D-slice image SI in the system 12. Thus, the pose estimation module 20 determines the orientation in the cardiac-centric coordinate system and the features of the slice shown in FIGS. 5 and 6.

During training, it is preferred to start with a 3D image sequence representing one or more heart chambers, together with the corresponding anatomical models for each chamber (See e.g., FIG. 5). The anatomical model of one chamber is defined for instance as a triangulated surface whose points are located at the 3D position of the chamber endocardium. As described above, the data generation device creates such pairs of 3D images and corresponding anatomical models.

The triangulated surface is preferably parameterized based on a cardiac-centric reference system built from the chamber geometry. For instance, considering the left ventricle (LV), three orthogonal axes of the reference system can be defined as the long axis of the left ventricle (line connecting the LV apex to the barycenter of the mitral annulus), the axis connecting the barycenter of the mitral annulus with the barycenter of the tricuspid valve, and a third axis orthogonal to the previous two.

Based on this reference system, triangulated surfaces derived from different 3D images are preferably parameterized in the same way. Also, based on this reference system, any cutting plane representing the plane of a 2D image (see e.g., the slice S in FIG. 5) could additionally be labeled depending on what parts of the chamber it intersects. The training set for the pose estimation module 20 is preferably a set of 'image, label'-pairs, where the image is obtained by intersecting the original 3D image with the cutting plane; and the label is obtained.

Figure 7:
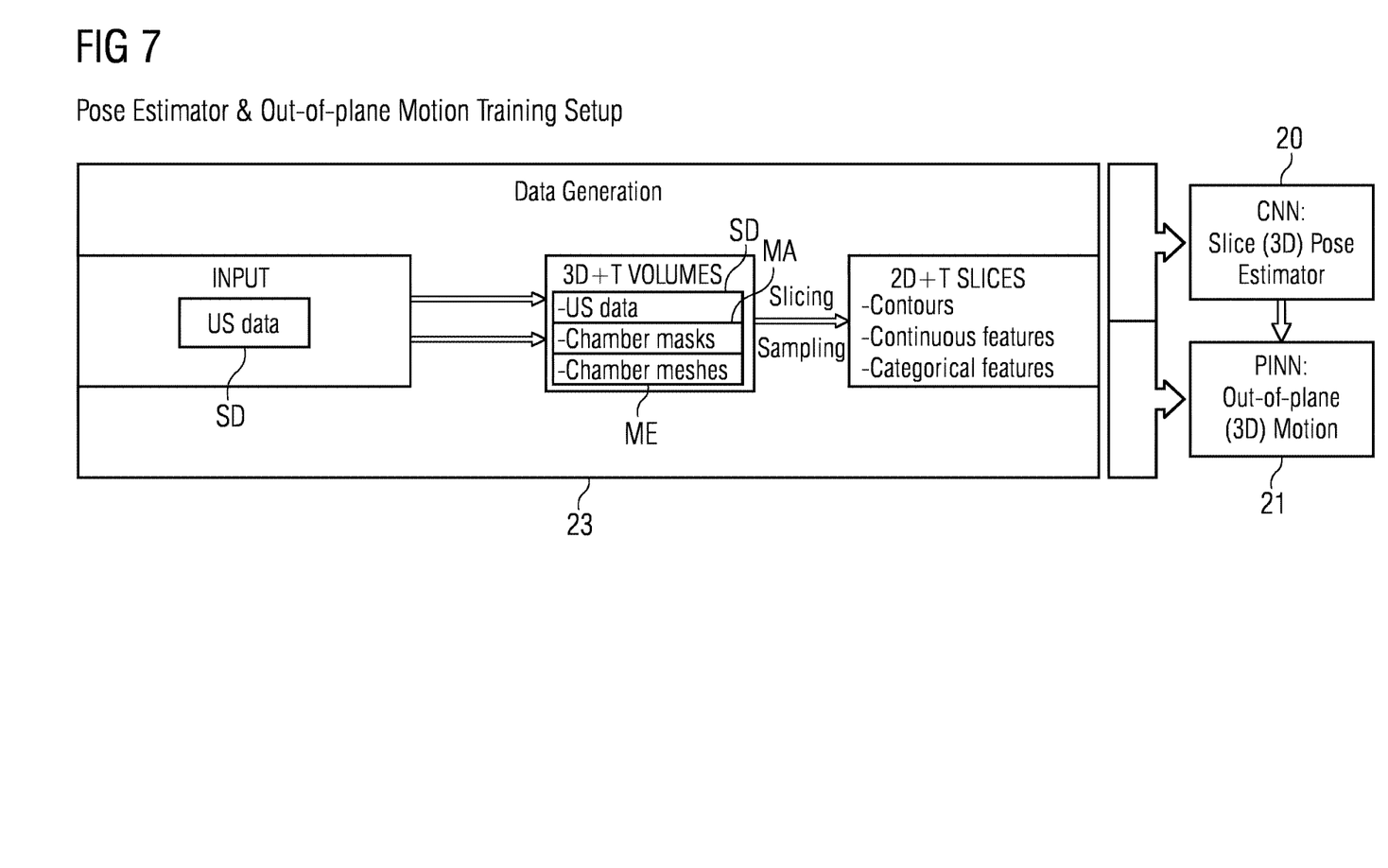
FIG. 7 depicts the process flow of a preferred manufacturing method according to one embodiment.

FIG. 7 depicts an alternative process flow of a preferred manufacturing method compared to FIG. 4. In contrast to FIG. 4, there are provided (received downloaded) multiple datasets of different 3D+time image sequences IS (here real ultrasound images: "US data"), each of the 3D+time image sequences IS showing a number of cycles of a beating heart.

In the shown case, the real 3D+time image sequence IS is used to generate corresponding 3D cardiac chamber mask MA and a 3D deformation field DF are generated from the input data. Furthermore, cardiac chamber meshes ME are created using the 3D cardiac chamber masks MA and the 3D deformation field DF.

After that, the method proceeds similar to FIG. 4: slicing and training.

Regarding the training of the 3D deformation estimation module 21, this module is trained in order to generate a 3D deformation field DF in the 3D neighborhood of any cardiac contour. The training input uses a given 2D image sequence and the associated cardiac contours and estimated slicing-pose (see FIG. 5).

According to a preferred embodiment, the training set is defined based on synthetically generated motion fields. In this case, one or more anatomical models representing one or more cardiac chambers are build based on statistical shape models or based on shape templates or using segmentation from images (see FIG. 5). The anatomical models are then deformed by applying a displacement field (a 3D deformation field DF) representing the motion of the heart chambers over one or multiple cardiac cycles. The displacement field can be defined based on analytical motion models, statistical motion models, or computational models. To each anatomical model, one or multiple motion models can be applied. This results in an arbitrarily large database of realistic 3D+time heart chamber geometries.

For each 3D+time chamber geometry, several cutting planes are preferably considered, representing the imaging plane of a 2D image (only one of them shown as slice S in FIG. 5). The intersection of the 3D+time chamber geometry and the cutting plane results in a 2D+time chamber contour, to which a 3D motion field is preferably associated.

Additionally, each point on the 2D+time contour is preferably also associated to its motion in the 2D cutting plane. This is the observable motion in the 2D imaging, that is used to determine 2D strain.

For each 2D+time contour, a 3D bounding box B is preferably defined (especially fixed in time), that contains the contour points over the entire time sequence and extends out of the cutting plane (i.e., the region of origins of arrows in FIG. 5). The problem is then preferably formulated as the estimation of the 3D motion of points in the bounding box B, given as input the observed (in-plane) motion of the contour points on the slice S. It is preferably solved by training a system to accept as input a bounding box B defined as described above, that can be discretized as a regular grid of voxels. Voxels corresponding to the position of points belonging to the 2D+time contour are associated with the observed (in-plane) motion field. Preferred ground truth labels are the values of the 3D+time motion field (i.e., the 3D deformation field) in all voxels of the bounding box B.

To regularize the problem, a PINN is preferred, solving the regression problem while respecting the underlying law of motion of an elastic body. The advantage of this approach is implicitly forcing the network to prefer solutions that satisfy global relationship valid in 3D space for bodies with a given mechanical behavior. Natural extensions of this approach include considering different motion laws in the PINN, such as hyperelastic or viscoelastic.

In a preferred embodiment, hybrid active and passive material laws can be considered, according to which the motion of the body is determined by the interplay of actively generated contraction and passive resistance to motion. In this embodiment, an additional input is preferably provided to the network in the form of a scalar field defined in the bounding box, and assuming nontrivial values in correspondence of the 2D+time contour points. This scalar field represent the time of activation of the cardiac muscle, a determinant of the cardiac motion. Time of activation could be derived for instance from ECG signals paired to the 2D images. In the training process, time of activation could be defined a priori or derived from the computational model used to generate the 3D motion.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other acts or elements. The mention of a "unit", a "module" or a "device" does not preclude the use of more than one unit or device.

The invention claimed is:

1. A system for heart strain determination, the system comprising:
   a computer configured to receive a series of 2D-slice images that have been recorded at different times of the cardiac cycle as input, to execute several modules, to pass intermediate result-data from an output of one module to an input of another module, and to output a result, the several modules including:
   a pose estimation module configured to estimate a slicing-pose, a position and orientation in space, of the inputted series of 2D-slice images in the heart,
   a 3D deformation estimation module configured to estimate a 3D deformation field from the series of 2D-slice images and the estimated slicing-pose, wherein the 3D deformation estimation module is a machine learning model that has been trained with results of the pose estimation module, and
   a strain measurement module configured to compute a heart strain measure from the 3D deformation field and a predefined definition for strain computation.

2. The system according to claim 1, wherein the pose estimation module is a convolutional neural network trained to estimate the pose of the series of 2D-slice images in the heart and/or the 3D deformation estimation module is a physics-informed neural network trained to estimate the 3D-deformation field from the series of 2D-slice images and the pose of these 2D-slice images.

3. The system according to claim 2, wherein the pose estimation module and the 3D deformation estimation module have been trained with a same data generation device.

4. The system according to claim 1, wherein the 3D-deformation estimation module is configured for additional determination of a statistical model for the deformations of the 3D deformation field and/or for estimation of cardiac contours.

5. The system according to claim 1 wherein the 3D-deformation estimation module is configured for estimation of a 3D deformation field on the 2D slice along the cardiac contours or along a 3D neighborhood of the contours.

6. The system according to claim 1, wherein the strain measurement module is a geometric computation module configured to receive as an input the 3D deformation field and to use the predefined definition for strain computation, wherein the strain measurement module is configured to calculate a linear strain as a relative change in length between two states.

7. The system according to claim 1 wherein the strain measurement module is a symmetric 3-tensor.

8. The system according to claim 1, wherein the pose estimation module or an additional detection module was trained for detecting cardiac contours within the 2D-slice images.

9. The system according to claim 1, wherein the pose estimation module and/or the 3D deformation estimation module have been trained with data generated by a data generation device comprising:
  a data-conditioning module configured to condition and output conditioned 3D+time image sequences of a heart, 3D cardiac chamber masks and cardiac chamber meshes to a slicing module, the data-conditioning module comprising a data interface and a generation module,
    a) wherein the conditioned 3D+time image sequences are based on images of a real heart, the data interface is configured for receiving scan data of a heart in form of 3D+time image sequences, and the generation module is configured to generate 3D cardiac chamber masks and cardiac chamber meshes based on the 3D scan data and 3D deformation fields determined from the 3D scan data, and/or
    b) wherein the conditioned 3D+time image sequences are based on synthetic conditioned 3D+time image sequences, the data interface is configured for receiving 3D deformation fields form a predefined library and predefined 3D cardiac chamber masks, and the generation module is configured for rendering the synthetic 3D+time image sequences from the 3D cardiac chamber masks and the 3D deformation fields,
  a slicing module configured to generate 2D-slice images from the 3D+time image sequences received from the data-conditioning module along a predefined plane, and
  a sampling module configured to sample features of interest onto slices.

10. The system according to claim 9, wherein both the pose estimation module and the 3D deformation estimation module based on neural networks trained with the 2D-slice images generated by the slicing module as training data and the 3D deformation fields, the cardiac chamber meshes, and the conditioned 3D+time image sequences as ground truth.

11. The system according to claim 9, wherein the conditioned 3D+time image sequences are based on the synthetic conditioned 3D+time image sequences, wherein the generation module is configured to render the synthetic 3D+time image sequences from the 3D cardiac chamber masks, the 3D deformation fields, and cardiac chamber meshes using a GauGAN or TecoGAN algorithm.

12. A method for heart strain determination, the method comprising:
  providing a series of 2D-slice images of a cross section of a heart that are recorded at different times,
  determining an evaluation of a slicing-pose of the 2D-slices by inputting the 2D-slices in a pose estimation module,
  determining a 3D-deformation field by inputting the series of 2D-slice images and the evaluated slicing-pose in a 3D-deformation estimation module, and
  determining a 3D-strain by inputting the determined 3D-deformation field in a measurement module.

13. The method according to claim 12, further comprising detecting cardiac contours within the 2D-slice images.

14. The method according to claim 13 wherein the cardiac contours are detected before determining the 3D-deformation field, wherein the 3D-deformation field is determined for the detected cardiac contours.

15. A method for manufacturing a system for heart strain determination, the method comprising:
  providing multiple datasets of different 3D+time image sequences, each of the 3D+time image sequences showing a number of cycles of a beating heart,
  providing 3D cardiac chamber masks and cardiac chamber meshes for respective ones of the 3D+time image sequences,
  slicing the 3D+time image sequences along a predefined plane to form a 2D-slice image and adding features to the 2D-slice image based on the 3D cardiac chamber mask and cardiac chamber mesh combined with this 3D+time image sequence,
  training a pose estimation module and/or a 3D deformation estimation module using the sliced 3D+time image sequences as training data and ground truths based on the 3D+time image sequences and the 3D cardiac chamber masks and the cardiac chamber meshes combined with the 3D+time image sequences.

16. The method of claim 15, wherein a data generation module trains the pose estimation module and/or the 3D deformation estimation module.

17. The method of claim 16, wherein a trained pose estimation module is used for training the 3D deformation estimation module.

18. The method of claim 15, wherein the 3D+time image sequences based on images of a real heart are received and the corresponding 3D deformation fields, the corresponding 3D cardiac chamber masks, and the cardiac chamber meshes are derived from the 3D+time image sequences.

19. The method of claim 15, wherein the 3D deformation fields are received form a predefined library and predefined 3D cardiac chamber masks are received, and the corresponding synthetic 3D+time image sequences are generated based on 3D deformation fields, the 3D cardiac chamber masks, and the cardiac chamber meshes.

20. The method of claim 19, wherein the cardiac chamber meshes are received, and the synthetic 3D+time image sequences are generated using a GauGAN or TecoGAN algorithm.

* * * * *

UNITED STATES PATENT AND TRADEMARK OFFICE
CERTIFICATE OF CORRECTION

| | |
|---|---|
| PATENT NO. | : 12,198,813 B2 |
| APPLICATION NO. | : 17/657208 |
| DATED | : January 14, 2025 |
| INVENTOR(S) | : Viorel Mihalef, Tiziano Passerini and Puneet Sharma |

It is certified that error appears in the above-identified patent and that said Letters Patent is hereby corrected as shown below:

On the Title Page

After Item (65) please add:
(30) Foreign Application Priority Data
April 12, 2021 (EP) ...........21167928

Signed and Sealed this
Twenty-eighth Day of October, 2025

John A. Squires
*Director of the United States Patent and Trademark Office*